United States Patent
Cedilote et al.

(10) Patent No.: US 7,429,589 B2
(45) Date of Patent: Sep. 30, 2008

(54) MONO-NITRATION OF AROMATIC COMPOUNDS VIA NITRATE SALTS

(75) Inventors: Miall Cedilote, Florence, SC (US); Thomas Patrick Cleary, Florence, SC (US); Pingsheng Zhang, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/712,359

(22) Filed: Feb. 27, 2007

(65) Prior Publication Data

US 2007/0255057 A1    Nov. 1, 2007

Related U.S. Application Data

(60) Provisional application No. 60/795,431, filed on Apr. 27, 2006.

(51) Int. Cl.
  *A61K 31/5375* (2006.01)
  *C07D 265/30* (2006.01)
(52) U.S. Cl. .................................. 514/237.8; 544/106
(58) Field of Classification Search .............. 514/237.8, 514/394, 385, 646, 393; 544/107
  See application file for complete search history.

(56) References Cited

U.S. PATENT DOCUMENTS 5,185,346 A    2/1993  Sanz et al.
7,087,761 B2 *  8/2006  Spurr ........................ 548/163

FOREIGN PATENT DOCUMENTS

WO    WO 01/97786    12/2001

OTHER PUBLICATIONS

Claus, et al., Justus Liebigs Annalen Der Chemie, vol. 274, pp. 285-304, (1893), XP009087333.
Claus, Herbabny, Justus Liebigs Annalen Der Chemie, vol. 265, pp. 364-378 (1891), XP009087334.
Kozhushkov, Yufit, De Meijere, Adv. Synth. Catal., vol. 347, pp. 255-265 (2005), XP002444253.
Forsyth, Pyman, J. Chem. Soc., pp. 2912-2924 (1926), XP009087330.
Kutnetsov, et al., Bull. Acad. Sci. USSR, Div. Chem. Sci., vol. 38, pp. 2142-2145, (1989), XP009087356.

* cited by examiner

*Primary Examiner*—Rita Desai
*Assistant Examiner*—John Mabry
(74) *Attorney, Agent, or Firm*—George W. Johnston; Patricia S. Rocha-Tramaloni

(57)    ABSTRACT

A method of nitrating a compound selected from the group consisting of

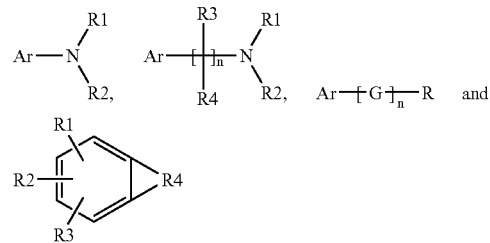

is provided.

1 Claim, No Drawings

MONO-NITRATION OF AROMATIC COMPOUNDS VIA NITRATE SALTS

PRIORITY TO RELATED APPLICATIONS

This application claims the benefit of U.S. Provisional Application No. 60/795,431, filed Apr. 27, 2006, which is hereby incorporated by reference in its entirety.

FIELD OF THE INVENTION

The present invention relates to the nitration of substrates that contain at least one basic nitrogen atom. Further the process includes the formation and isolation of nitrate salts formed from the substrates and nitric acid and thereafter the nitration of the salts under acidic conditions. In general therefore, the present invention relates to a general method for mono-nitration of aromatic compounds bearing a basic nitrogen atom and in a more specific embodiment to a process for the preparation of 4-morpholino-2-nitroanisole.

BACKGROUND OF THE INVENTION

Nitration of aromatic nucleus is one of the most basic reactions in organic chemistry and is widely used for preparing nitro aromatic compounds. However, the reaction is notorious for several reasons and most pharmaceutical manufacturers are discouraged to carry out large scale nitration in-house. Safety issues are the primary concerns. Two major factors contribute to the safety aspect of the reaction. The first is the reaction itself. The most commonly used nitrating reagent is a mixture of concentrated nitric acid and sulfuric acid. Both of them are strong oxidizers. Although there are alternative nitrating reagents, the majority of them generate nitric acid or other highly reactive intermediates in situ. The nitration reaction is usually highly exothermic and has high risk of runaway to explosion upon mishandling of the process or equipment failures. The second is the nitrated products. Most of them have low thermo and/or impact stabilities and release large quantity of energy upon decomposition (for instance, TNT, trinitrotoluene, is a powerful explosive). As a result, extra precautions have to be taken when nitration is carried out, which include special equipment (e.g. bunkered reactors) and intensive training of personnel. Besides safety problems, side reactions are another concern. For instance, over-nitration could occur whenever the nitrating reagents are overcharged. Regioisomer formation and reactions at side-chains are common. Therefore, the development of new nitration methods that lead to safer nitration processes and better control of chemistry is still an important research goal.

SUMMARY OF THE INVENTION

In accordance with this invention, it has been discovered that this process is applicable to a variety of compounds. In theory, any aromatics that can be nitrated under conventional conditions and contain a basic nitrogen atom can be nitrated using this protocol. Some examples are listed in Table 1 through Table 4. For all the examples listed in tables 1 through 4, the nitration was carried out by adding a solution or suspension of the nitrate salt to approximately 10 equivalents of concentrated sulfuric acid. The substrates that can be covered in this invention are summarized in the following groups.

A. Aniline derivatives that have general structures of 6, where Ar is a nitratable aromatic ring, $R_1$ and $R_2$ are hydrogen, alkyl or aromatic groups. Some examples are listed in Table 1.

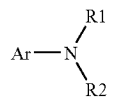

6

B. Aromatic compounds have general structure of 7, where Ar is a nitratable aromatic ring, $R_1$, $R_2$, $R_3$, and $R_4$ are hydrogen, alkyl or aromatic groups, and n is an integer from 1 to 12. Some examples are listed in Table 2.

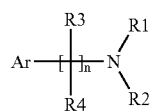

7

C. Aromatic compounds have general structure of 8, where Ar is a nitratable aromatic ring, G are suitable atoms or groups (e.g. $CR_1R_2$, O, S, SO, $SO_2$, etc), R is a heterocyclic ring or other groups bearing a basic nitrogen atom. Some examples are listed in Table 3.

8

D. Fused-ring aromatic compounds have general structure of 9, where the benzene ring is fused with a heterocyclic ring that bears a basic nitrogen atom, $R_1$, $R_2$, and $R_3$ can be hydrogen or other groups that can tolerate conventional nitration conditions. Some examples are listed in Table 4.

TABLE 1

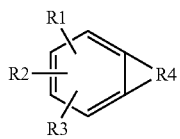

| Entry | Substrate | Structure of Salt | Nitrated Product | Yield: Salt Formation | Yield: Nitration |
|---|---|---|---|---|---|
| 1 | (structure) | S-1 | N-1 | 93% | 93% |

TABLE 1-continued

General structure:
R1, R2, R3, R4 substituents on benzene ring

| Entry | Substrate | Structure of Salt | Nitrated Product | Yield: Salt Formation | Yield: Nitration |
|---|---|---|---|---|---|
| 2 | 4-bromo-N,N-dimethylaniline | S-2: 4-bromo-N,N-dimethylanilinium nitrate | N-2: 4-bromo-3-nitro-N,N-dimethylaniline | 98% | 96% |
| 3 | 4-tert-butyl-N,N-dimethylaniline | S-3: 4-tert-butyl-N,N-dimethylanilinium nitrate | N-3: 4-tert-butyl-3-nitro-N,N-dimethylaniline | 99.4% | 94.6% |
| 4 | N,N-dimethylaniline | S-4: N,N-dimethylanilinium nitrate | N-4: 3-nitro-N,N-dimethylaniline (75%); N-5: 4-nitro-N,N-dimethylaniline (25%) | 96.5% | 89% |
| 5 | 3-methyl-N,N-dimethylaniline | S-5: 3-methyl-N,N-dimethylanilinium nitrate | N-6: 3-methyl-4-nitro-N,N-dimethylaniline | 99.9% | 93% |

TABLE 1-continued

| Entry | Substrate | Structure of Salt | Nitrated Product | | Yield: Salt Formation | Yield: Nitration |
|---|---|---|---|---|---|---|
| 6 | (structure) | S-6 | N-7 | | 94.5% | 88% |
| 7 | (structure) | S-7 | N-8 (66%) | N-9 (34%) | 99.9% | 95% |
| 8 | (structure) | S-8 | N-10 | N-11 | 98.9% | 92% |
| 9 | (structure) | S-9 | N-12 | | 97% | 95% |
| 10 | (structure) | S-10 | N-13 | | 97% | 91% |

TABLE 1-continued

[Structure: benzene ring with R1, R2, R3, R4 substituents]

| Entry | Substrate | Structure of Salt | Nitrated Product | Yield: Salt Formation | Yield: Nitration |
|---|---|---|---|---|---|
| 11 | aniline (NH₂-phenyl) | S-11 (anilinium nitrate, +NH₃ NO₃⁻) | N-14: 3-nitroaniline (50%); N-15: 4-nitroaniline (47%); N-16: 2-nitroaniline (3%) | 98% | 95% |
| 12 | 4-chloro-2-methylaniline | S-12 (corresponding ammonium nitrate) | N-17: 5-amino-2-chloro-4-methyl-nitrobenzene | 96% | 96% |

TABLE 2

| Entry | Substrate | Structure of Salt | Nitrated Product | Yield: Salt Formation | Yield: Nitration |
|---|---|---|---|---|---|
| 1 | N,N-dimethylbenzylamine | S-13 (ammonium nitrate salt) | N-18: 3-nitro isomer (67%); N-19: 4-nitro isomer (25%); N-20: 2-nitro isomer (8%) | ~100% (oil) | 95% |

TABLE 2-continued

| Entry | Substrate | Structure of Salt | Nitrated Product | | Yield: Salt Formation | Yield: Nitration |
|---|---|---|---|---|---|---|
| 2 | (4-methoxybenzylamine) | S-14 | N-21 | | 95% | 94% |
| 3 | (3-chlorophenethylamine) | S-15 | N-22 (55%) | N-23 (45%) | 99% | 89% |

TABLE 3

| Entry | Substrate | Structure of Salt | Nitrated Product | Yield: Salt Formation | Yield: Nitration |
|---|---|---|---|---|---|
| 1 | (4,4-dimethyl-2-phenyloxazoline) | S-16 | N-24 | 96% | 93% |
| 2 | (2-(p-tolyl)pyridine) | S-17 | N-25 | 99% | 95% |
| 3 | (2-phenyl-4,5-dihydroimidazole) | S-18 | N-26 | 91% | 90% |

TABLE 3-continued

| Entry | Substrate | Structure of Salt | Nitrated Product | | | Yield: Salt Formation | Yield: Nitration |
|---|---|---|---|---|---|---|---|
| 4 | (imidazole with SO2-tolyl) | S-19 | N-27 | | | 90% | 91% |
| 5 | 2-phenylimidazole | S-20 | N-28 | | | 99% | 96% |
| 6 | 1-benzylimidazole | S-21 | N-29 | N-30 | N-31 | 92% | 92% |

TABLE 4

| Entry | Substrate | Structure of Salt | Nitrated Product | | Yield: Salt Formation | Yield: Nitration |
|---|---|---|---|---|---|---|
| 1 | 2-methylbenzoxazole | S-22 | N-32 (76%) | N-33 (24%) | 98% | 91% |
| 3 | 5,6-dimethylbenzimidazole | S-23 | N-34 | | 97.3% | 99% |

TABLE 4-continued

| Entry | Substrate | Structure of Salt | Nitrated Product | Yield: Salt Formation | Yield: Nitration |
|---|---|---|---|---|---|
| 4 | (6-methoxyquinoline) | S-24 | N-35 | 88% | 96% |

The salts of the substrates of tables 1-4 could be generally prepared by adding 1.0 eq. of 70% nitric acid to a solution of the substrate at <20° C. TBME was used as reaction solvent for the substrates soluble in it. For the substrates that were less soluble in TBME, a second solvent was added to help the solubility. The solvent combinations used for the reaction included TBME/THF, TBME/acetonitrile, TBME/ethyl acetate, etc. For the salts that precipitated out of the solutions during the salt formation, the isolation was achieved by filtration and drying under vacuum at ambient temperature. For the salts that did not completely precipitate out from the solution, acetonitrile was added until homogeneous solutions were formed. The solutions were then dried over MgSO$_4$, filtered, and concentrated to afford the solid salts.

The nitration of a salt was carried out by adding a solution or suspension of the salt to excess amount of sulfuric acid at <10° C. Solvents used for the reaction included dichloromethane, nitromethane, and others that are inert to the reaction mixture. Upon the completion of the reaction the mixture was diluted by adding the acid layer to water at <20° C. The diluted mixture was then basified to pH 6-11 by adding a base, such as aqueous ammonia solution, aqueous potassium carbonate, aqueous sodium carbonate, or aqueous sodium bicarbonate, etc. In most of the cases, the product precipitated out at this point. The solid product was filtered, washed with water, and dried under vacuum at around 50° C. overnight to give the nitrated product. In the cases in which the product precipitated out as an oil, the mixture was extracted with a solvent (e.g. dichloromethane, ethyl acetate, etc.). The organic solution was then washed with water, dried over MgSO$_4$, filtered, and concentrated to give the crude product.

Application of the nitration method resulted in an invention of a new process for the preparation of 4-Morpholino-2-nitroanisole (4), a key intermediate for a drug candidate currently being developed to treat depression (WO 01/97786). The process is summarized in Scheme 1.

There are several major advantages of the new process over the original one disclosed in the above application, which include:

1) A simplified process. With the precipitation of 5 directly from the extract of crude product from the first step, the isolation of free base of 5 was avoided.

2) Increased robustness. The salt 5 contains an exact 1:1 ratio of substrate (free base of 5) to nitric acid. Therefore, the formation of the dinitrated impurity became unlikely. This process eliminated the necessity for the precise measurement and charge of nitric acid, and so released burden on process operation.

3) Improved safety profile. The process eliminated the operation of adding solid free base of 5 to concentrated sulfuric acid (very risky operation on large scale because the process is strongly exothermic). Instead, a solution of 5 in dichloromethane was added to sulfuric acid. The addition process could be easily controlled to prevent excessive heat generation. The process also eliminated the operation of mixing 70% nitric acid with concentrated sulfuric acid.

4) Reduced waste generation and improved process capacity. The use of 5 in the process made it possible to reduce the sulfuric acid charge by 60%, which led to the reduction of waste generated in the process by 40% and capacity increase by 30%.

5) Significant yield improvement. The overall yield obtained using the new process was 92% while that of the original process was only 58%, a 59% improvement.

As aromatic groups there are contemplated aryl groups.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heterocyclic group" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrollidin-3-yl; imidazol-4-yl; pyrazol-3-yl; morpholin-4-yl and the like.

"Hetero atom" means an atom selected from N, O and S.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

The process of the present invention can be carried out as set forth in the following schemes.

Scheme 1

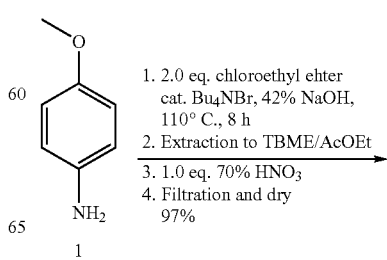

1. 2.0 eq. chloroethyl ehter cat. Bu$_4$NBr, 42% NaOH, 110° C., 8 h
2. Extraction to TBME/AcOEt
3. 1.0 eq. 70% HNO$_3$
4. Filtration and dry
97%

1

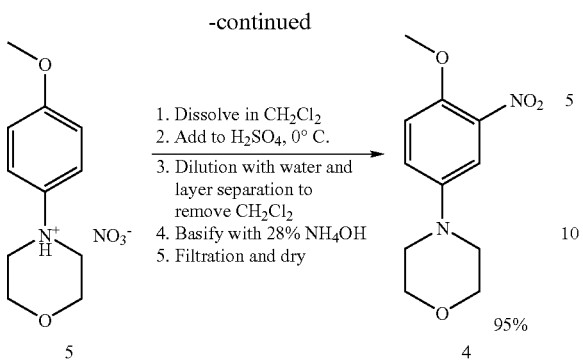

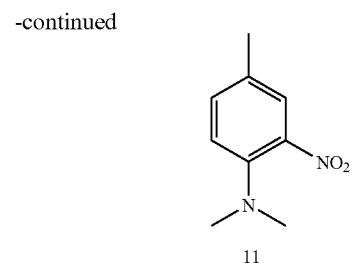

Nitration of the salts could also be carried out under different conditions. For instance, the reaction could be conducted by adding acetyl chloride to a solution of a nitrate salt in dichloromethane. In some cases, different products were obtained using different methods. For example, when the nitration of 5 was carried out by adding its solution to sulfuric acid the product was 4 (Scheme 1). However, when the nitration was conducted by adding 2.0 eq of acetyl chloride to a solution of 5 in acetic acid product 10 was isolated in 91% yield. Another example is demonstrated in Scheme 2. These examples indicated that the regioselectivity for nitration of the nitrate salts of aniline derivatives could be controlled by selecting different conditions.

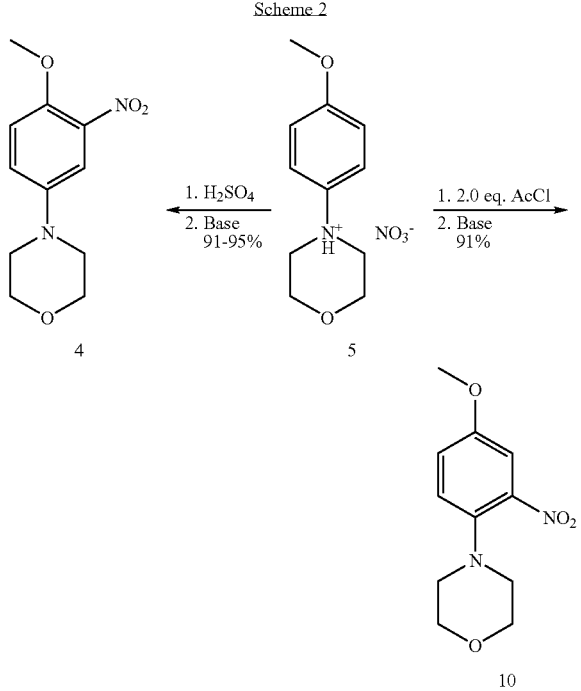

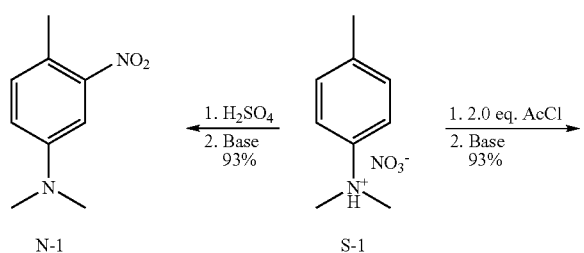

Besides sulfuric acid, other acids can also be used for the nitration of the nitrate salts. This was exemplified by the nitration of S-1 using trifluoroacetic acid, a solution of methanesulfonic acid in methylene chloride, and pure methanesulfonic acid. The results are summarized in Table 5.

TABLE 5

| Substrate | Acid | Conditions | Yield | Product |
|---|---|---|---|---|
| S-1 | Trifluoroacetic acid | 0° C., 1 h | 94% | 11 |
| S-1 | Methaneslfonic acid In CH$_2$Cl$_2$ solution | 0° C., 4 h | 92% | 11 and N-1 with a ratio of 93/7 |
| S-1 | Methaneslfonic acid | 17° C., | 91% | 11 and N-1 with a ratio of 75/25 |

DETAILED DESCRIPTION OF THE INVENTION

The present invention relates to a nitration process for aromatic compounds selected from the group consisting of

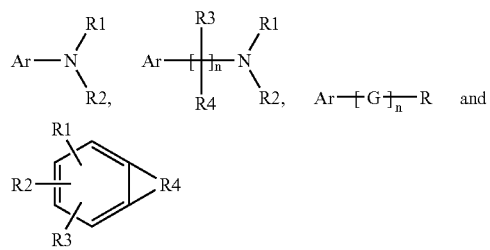

wherein

Ar is a nitratable aromatic ring, $R_1$, $R_2$, $R_3$, and $R_4$ are hydrogen, alkyl or an aromatic groups, G is selected from the group consisting of $CR_1R_2$, O, S, SO and $SO_2$, R is a heterocyclic ring or other groups bearing a basic nitrogen atom and n is an integer from 1 to 12 which comprises forming and isolating a nitrate salt of the starting material after reaction of the starting material with nitric acid and thereafter adding a solution or suspension of the nitrate salt to an acid. The isolated nitrate salts consist of 1:1 ratio of nitric acid and the amine substrates. Thus, over-nitration and under-nitration can be easily prevented in the nitration process, which is otherwise difficult to control on large scale manufacturing processes.

As aromatic rings/groups there are contemplated aryl groups.

The following examples and references are provided to aid the understanding of the present invention, the true scope of which is set forth in the appended claims.

EXAMPLE 1

Morpholinoanisole, Nitric Acid Salt (5)

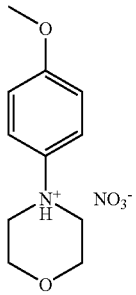

A dry, clean, 1 L, 4-neck round bottom flask, equipped with a mechanic stirrer and a nitrogen inlet, was charged with 20 g (162.3 mMol) of p-anisidine, 48 g (336 mMol) of 2-chloroethyl ether, 1.04 g (3.2 mMol) of tetrabutylammonium bromide, and 77 g of 42% sodium hydroxide solution. The mixture was refluxed at around 110° C. for about 8 h. After confirming the completion of the reaction, the mixture was cooled to 20° C. and extracted with 50 mL TBME and 50 mL ethyl acetate, respectively. The combined organic solution was washed with 80 mL water. The organic solution was cooled to 0±5° C. and to it was slowly added 14.6 g (162.3 mMol) 70% $HNO_3$. A heavy precipitation was formed at the late stage of the addition. After the addition the batch was aged for at least 1 h. The solid was filtered, washed with 40 mL of TBME, and dried under vacuum at 45° C. overnight to give 40.2 g (97%) 5 as a tan solid.

EXAMPLE 2

4-Morpholino-2-nitroanisole (4)

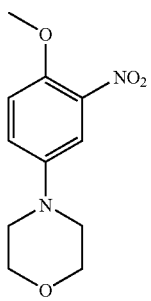

A dry, clean, 250 mL, 4-neck round bottom flask, equipped with a mechanic stirrer and a nitrogen inlet, was charged with 80 g (815 mMol) of 95% sulfuric acid. The acid was cooled to ~0° C. A solution of 20 g (78 mMol) 5 in 125 mL dichloromethane was slowly added to the acid while maintaining batch temperature at 0±5° C. After the addition the mixture was stirred for 30 minutes. The agitation was stopped and the bottom acid layer was separated. The acid solution was slowly added to 200 mL water while maintaining the temperature at <10° C. To this diluted acid solution was then slowly added 190 mL 28% $NH_4OH$ solution while maintaining the temperature at <10° C. At the end of the addition the pH of the mixture should be higher than 10. The batch was aged at 5±5° C. for 1 h. The solid was filtered, washed with 50 mL water, and dried under vacuum at 45° C. overnight to give 17.5 g (94% yield) of 4 as an orange solid.

EXAMPLE 3

Aniline, Nitric Acid Salt (S-11)

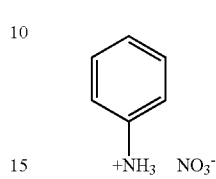

A solution of aniline (10 g, 107 mMol) in 100 mL TBME was cooled to 0±5° C. To this solution was added 70% nitric acid (9.7 g, 107 mMol) while maintaining the temperature at <20° C. After the addition the mixture was agitated at 0±5° C. for approximately 1 h. The solid was filtered, washed with TBME, and dried under house vacuum at ambient temperature overnight to give 16.4 g (98%) of the title compound.

Compounds S-9, S-12, S-14, S-15, S-16, S-22 were prepared using the same procedure.

EXAMPLE 4 p-anisidine, Nitric Acid Salt (S-10)

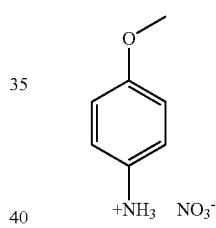

A solution of p-anisidine (10 g, 81.2 mMol) in 80 mL TBME and 20 mL THF was cooled to 0±5° C. To this solution was added 70% nitric acid (7.3 g, 81.2 mMol) while maintaining the temperature at <20° C. After the addition the mixture was agitated at 0±5° C. for approximately 1 h. The solid was filtered, washed with TBME, and dried under house vacuum at ambient temperature overnight to give 14.6 g (97%) of the title compound.

Compounds S-19, S-21 were prepared using the same procedure.

EXAMPLE 5

N,N-dimethylbenzylamine, Nitric Acid Salt (S-13)

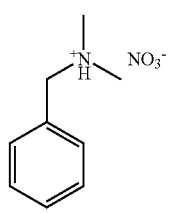

A solution of N,N-dimethylbenzylamine (10 g, 74 mMol) in 80 mL TBME and 20 mL THF was cooled to 0±5° C. To this solution was added 70% nitric acid (6.7 g, 74 mMol) while maintaining the temperature at <20° C. After the addition the mixture was agitated at 0±5° C. for approximately 1 h. Acetonitrile was added to the reaction mixture until a homogeneous solution was formed. The solution was dried over MgSO$_4$, filtered, and concentrated to give 14.7 g (100%) of the title compound.

Compounds S-1, S-2, S-3, S-4, S-5, S-6, S-7, S-8, S-17 were prepared using the same procedure.

EXAMPLE 6

Phenyl-2-imidazoline, Nitric Acid Salt (S-18)

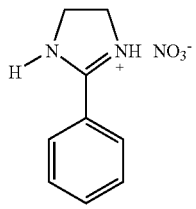

A suspension of 2-phenyl-2-imidazoline (10 g, 68.4 mMol) in 100 mL TBME and 50 mL acetonitrile was cooled to 0±5° C. To this suspension was added 70% nitric acid (6.2 g, 68.4 mMol) while maintaining the temperature at <20° C. After the addition the mixture was agitated at 0±5° C. for approximately 1 h. The solid was filtered, washed with TBME, and dried under house vacuum at ambient temperature overnight to give 13.4 g (91%) of the title compound.

Compounds S-20, S-23, S-24 were prepared using the same procedure.

EXAMPLE 7

4,N,N-Trimethyl-3-nitroaniline (N-1)

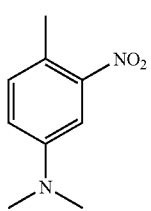

A solution of S-1 (3 g, 15.1 mMol) in 25 mL dichloromethane was slowly added to cold 95% sulfuric acid (14.8 g, 151 mMol) while maintaining the batch temperature at 0±5° C. After the addition the mixture was agitated at 0±5° C. for approximately 3 h. The agitation was stopped and the bottom acid layer was slowly transferred to 30 mL of water while maintaining the temperature at <20° C. To the diluted reaction mixture was slowly added ammonium hydroxide solution at <20° C. until pH>10. Precipitation formed. The mixture was aged at <20° C. for approximately 1 h. The solid was filtered, washed with water, and dried under house vacuum at ~45° C. overnight to give 2.54 g (93%) of the title compound.

Compounds N-3, N-6, N-4/N-5, N-8/N-9, N-10/N-11, N-17, N-32/N-33 were prepared using the same procedure.

EXAMPLE 8

2-(4-nitrophenyl)imidazole (N-28)

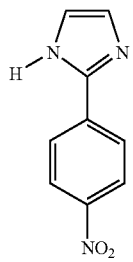

A suspension of S-20 (4 g, 19.3 mMol) in 30 mL dichloromethane was slowly added to cold 95% sulfuric acid (18.9 g, 193 mMol) while maintaining the batch temperature at 0±5° C. After the addition the mixture was agitated at 0±5° C. for approximately 3 h. The agitation was stopped and the bottom acid layer was slowly transferred to 40 mL of water while maintaining the temperature at <20° C. To the diluted reaction mixture was slowly added ammonium hydroxide solution at <20° C. until pH>10. Precipitation formed. The mixture was aged at <20° C. for approximately 1 h. The solid was filtered, washed with water, and dried under house vacuum at ~45° C. overnight to give 3.5 g (96%) of the title compound.

Compounds N-24, N-26, N-27 N-34, N-35 were prepared using the same procedure.

EXAMPLE 9

Methoxy-3-nitro-N-methylaniline (N-12)

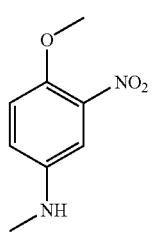

A solution of S-9 (4 g, 20 mMol) in 40 mL dichloromethane was slowly added to cold 95% sulfuric acid (20 g, 200 mMol) while maintaining the batch temperature at 0±5° C. After the addition the mixture was agitated at 0±5° C. for approximately 3 h. The agitation was stopped and the bottom acid layer was slowly transferred to 40 mL of water while maintaining the temperature at <20° C. To the diluted reaction mixture was slowly added ammonium hydroxide solution at <20° C. until pH was approximately 7. The mixture was extracted twice with dichloromethane. The combined organic solution was washed with brine, dried over MgSO$_4$, filtered, and concentrated to give 3.46 g (95%) of the title compound.

Compound N-9 was also prepared using the same procedure.

Example 10

Methoxy-3-nitroaniline (N-13)

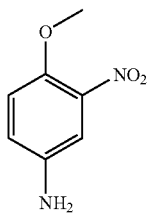

A suspension of S-10 (4 g, 21.5 mMol) in 40 mL dichloromethane was slowly added to cold 95% sulfuric acid (21 g, 215 mMol) while maintaining the batch temperature at 0±5° C. After the addition the mixture was agitated at 0±5° C. for approximately 3 h. The agitation was stopped and the bottom acid layer was slowly transferred to 40 mL of water while maintaining the temperature at <20° C. To the diluted reaction mixture was slowly added ammonium hydroxide solution at <20° C. until pH was 6-11. The mixture was extracted twice with dichloromethane. The combined organic solution was washed with brine, dried over MgSO$_4$, filtered, and concentrated to give 3.3 g (91%) of the title compound.

Compounds N-2, N-9, N-14/N-15/N-16, N-29/N-30/N-31, N-22/N-23, N-21 were prepared using the same procedure.

EXAMPLE 11

Morpholino-3-nitroanisole (10)

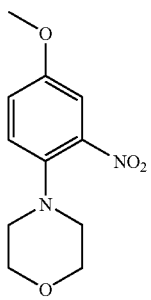

To a solution of 5 (2 g, 7.8 mMol) in 5 mL acetic acid was slowly added acetyl chloride (1.6 g, 15.6 mMol) at ambient temperature. The mixture was stirred for approximately 30 min. The reaction mixture was slowly added to cold ammonium hydroxide solution at <20° C. The mixture was then aged for about 1 h. The solid was filtered, washed with water, and dried under vacuum at 45° C. overnight to give 1.7 g (91% yield) of 10.

EXAMPLE 12

4,N,N-Trimethyl-2-nitroaniline (11)

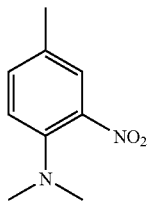

To a solution of S-1 (2 g, 10.1 mMol) in 10 mL dichloromethane was slowly added acetyl chloride (1.6 g, 15.6 mMol) at around 0° C. The mixture was stirred for approximately 2 h. The reaction mixture was basified to pH>10 by adding ammonium hydroxide solution at <20° C. The mixture was extracted twice with dichloromethane. The combined organic solution was washed with brine, dried over MgSO$_4$, filtered, and concentrated to give 1.7 g (93%) of 11.

EXAMPLE 13

Nitration of S-1 in Trifluoroacetic Acid

A solution of S-1 (4 g, 20.2 mMol) in 45 g dichloromethane was slowly added to trifluoroacetic acid (23 g, 202 mMol) while maintaining the batch temperature at 0±5° C. After the addition the mixture was agitated at 0±5° C. for approximately 1 h. The mixture was slowly transferred to 40 mL of water while maintaining the temperature at <20° C. To this mixture was slowly added 28% ammonium hydroxide solution at <20° C. until pH>10. The organic phase was separated and the aqueous phase was extracted with 48 g of methylene chloride. The combined organic solution was washed with brine and then concentrated to dryness on a rotavapor to give 3.44 g (94%) 11.

EXAMPLE 14

Nitration of S-1 in a Solution of Methanesulfonic Acid in Methylene Chloride A solution of S-1 (4 g, 20.2 mMol) in 22 g dichloromethane was slowly added to a mixture of 19 g of methanesulfonic acid and 22 g of dichloromethane while maintaining the batch temperature at 0±5° C. After the addition the mixture was agitated at 0±5° C. for approximately 4 h. The mixture was slowly transferred to 40 mL of water while maintaining the temperature at <20° C. To this mixture was slowly added 28% ammonium hydroxide solution at <20° C. until pH>10. The organic phase was separated and the aqueous phase was extracted with 55 g of methylene chloride. The combined organic solution was washed with brine and then concentrated to dryness on a rotavapor to give 3.41 g (92%) product as a mixture of 11 and N-1 with a ratio of approximately 93:7.

EXAMPLE 15

Nitration of S-1 in Methanesulfonic Acid

Solid S-1 (4 g, 20.2 mMol) was slowly added to 19 g of methanesulfonic acid while maintaining the batch temperature at 17±5° C. After the addition the mixture was agitated at 17±5° C. for approximately 1 h. The mixture was slowly transferred to 40 mL of water while maintaining the temperature at <20° C. To this mixture was slowly added 28% ammonium hydroxide solution at <20° C. until pH>10. The mixture was extracted with 43 g of dichloromethane. The organic phase was separated and the aqueous phase was extracted with 29 g of methylene chloride. The combined organic solution was washed with brine and then concentrated to dryness on a rotavapor to give 3.22 g (91%) product as a mixture of 11 and N-1 with a ratio of approximately 75:25.

What is claimed:
1. A process to produce a compound of the formula
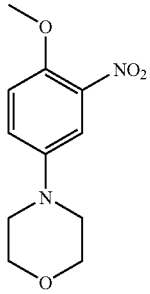
which comprises
(a) reacting a compound of the formula
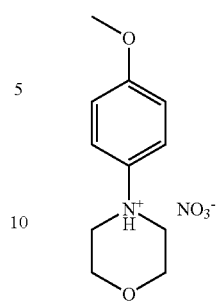
with sulfuric acid and after dilution with water
(b) treating the solution with base to reach a pH of greater than 10.
* * * * *